(12) United States Patent
Tanida

(10) Patent No.: US 11,621,054 B2
(45) Date of Patent: Apr. 4, 2023

(54) METHOD AND APPARATUS FOR PREPROCESSING OF BINDING FREE ENERGY CALCULATION, AND BINDING FREE ENERGY CALCULATION METHOD

(71) Applicant: FUJITSU LIMITED, Kawasaki (JP)

(72) Inventor: Yoshiaki Tanida, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 488 days.

(21) Appl. No.: 16/734,459

(22) Filed: Jan. 6, 2020

(65) Prior Publication Data
US 2020/0258594 A1  Aug. 13, 2020

(30) Foreign Application Priority Data
Feb. 8, 2019 (JP) ............... JP2019-021614

(51) Int. Cl.
*G16B 15/30* (2019.01)
*G16C 20/40* (2019.01)
*G16C 20/50* (2019.01)
*G16C 20/00* (2019.01)

(52) U.S. Cl.
CPC ............ *G16B 15/30* (2019.02); *G16C 20/40* (2019.02); *G16C 20/50* (2019.02); *G16C 20/00* (2019.02)

(58) Field of Classification Search
CPC .................................................. G16B 15/30
USPC ............................................ 713/11; 703/11
See application file for complete search history.

(56) References Cited

U.S. PATENT DOCUMENTS

| | | | |
|---|---|---|---|
| 2010/0267699 A1* | 10/2010 | Bradbuury et al. | C07C 1487/04 514/218 |
| 2011/0059043 A1* | 3/2011 | Barnes et al. | C07D 243/24 424/85.4 |
| 2017/0039314 A1* | 2/2017 | Bremel et al. | |

FOREIGN PATENT DOCUMENTS

| JP | 2017-91179 A | 5/2017 |
|---|---|---|
| WO | 2003/038672 A1 | 5/2003 |

OTHER PUBLICATIONS

Chodera, John D., "Alchemical free energy methods for drug discovery: progress and challenges", Current Opinion in Structural Biology, 21(2), pp. 150-160, Apr. 2011.

(Continued)

*Primary Examiner* — Thinh T Nguyen
(74) *Attorney, Agent, or Firm* — Fujitsu Patent Center

(57) ABSTRACT

A method is performed by a computer for a preprocessing for calculating binding free energy between a first substance and a second substance. The method includes: obtaining a binding structure of the first substance and the second substance under a condition where the second substance is constrained such that a binding state of the second substance to the first substance is maintained in a predetermined state; and then, based on the obtained binding structure, obtaining the binding structure under a condition where the second substance is not constrained.

13 Claims, 10 Drawing Sheets

(56) References Cited

OTHER PUBLICATIONS

Gallicchio, Emilio et al., "Recent Theoretical and Computational Advances for Modeling Protein-Ligand Binding Affinities", BioMaPS Institute for Quantitative Biology and Department of Chemistry and Chemical Biology, Rutgers Univ., pp. 1-43, Feb. 17, 2011.
Lee, Michael S. et al., "Calculation of Absolute Protein-Ligand Binding Affinity Using Path and Endpoint Approaches", Biophysical Journal, vol. 90, pp. 864-877, Feb. 2006.
Karlberg, Tobias et al., "Structural Basis for the Interaction between Tankyrase-2 and a Potent Wnt-Signaling Inhibitor", Journal of Medical Chemistry Brief Article, 53, pp. 5352-5355, 2010.

\* cited by examiner

METHOD AND APPARATUS FOR PREPROCESSING OF BINDING FREE ENERGY CALCULATION, AND BINDING FREE ENERGY CALCULATION METHOD

CROSS-REFERENCE TO RELATED APPLICATION

This application is based upon and claims the benefit of priority of the prior Japanese Patent Application No. 2019-21614, filed on Feb. 8, 2019, the entire contents of which are incorporated herein by reference.

FIELD

The embodiment discussed herein is related to a preprocessing method, a preprocessing apparatus for binding free energy calculation, and a binding free energy calculation method.

BACKGROUND

In recent years, various simulations using computers have been carried out for the purpose of reducing enormous costs and labor required for drug discovery. In the drug discovery using computers, it is important to accurately calculate and predict binding free energy between a target molecule such as protein involved in a target disease (disease to be targeted) and a candidate molecule serving as a candidate for a pharmaceutical product.

As a method for calculating binding free energy between a target molecule and a candidate molecule by using a computer, for example, an alchemical pathway calculation method of calculation along a virtual (alchemical) thermodynamic cycle is known as a method with high accuracy (see, for example, John D. Chodera et al., "Alchemical free energy methods for drug discovery: Progress and challenges", Current Opinion in Structural Biology, 2011.21, p. 150-160).

However, in the method such as the alchemical pathway calculation method, when a binding state of the candidate molecule to the target molecule is changed during sampling for calculating the binding free energy, there has been a case where quantitative prediction of the binding free energy is impossible.

In one aspect, it is an object of the present disclosure to provide a preprocessing method, a preprocessing apparatus, and a preprocessing program for binding free energy calculation, and a binding free energy calculation method that are capable of improving calculation accuracy of the binding free energy even when a binding state between substances easily changes.

SUMMARY

According to an aspect of the embodiments, a method is performed by a computer for a preprocessing for calculating binding free energy between a first substance and a second substance. The method includes: obtaining a binding structure of the first substance and the second substance under a condition where the second substance is constrained such that a binding state of the second substance to the first substance is maintained in a predetermined state; and then, based on the obtained binding structure, obtaining the binding structure under a condition where the second substance is not constrained The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Drug discovery means a process of designing a pharmaceutical product. The drug discovery is carried out, for example, in the following order.

(1) Target molecule determination
(2) Search for a lead compound or the like
(3) Physiological activity assay
(4) Safety and toxicity test In searching a lead compound or the like (a lead compound and a compound derived from the lead compound), it is important to accurately evaluate interaction between each of a large number of lead compounds, or the like (candidate molecules) and a target molecule.

Designing a pharmaceutical product by using a computer may be referred to as information technology (IT) drug discovery in some cases. Although technology of IT drug discovery is available for all drug discovery, it is particularly useful to use the technology of IT drug discovery for search for a lead compound or the like to shorten a period of time required for the drug discovery and to improve a success probability of the drug discovery.

The technology disclosed in the present disclosure may be used, for example, to search a lead compound or the like that is expected to have high pharmacological activity.

(Preprocessing Method of Binding Free Energy Calculation)

The preprocessing method of binding free energy calculation disclosed in the present disclosure is performed by using a computer, and is a method for obtaining a binding structure of a first substance and a second substance, which is an initial structure of binding free energy calculation between the first substance and the second substance. In the preprocessing method of the binding free energy calculation disclosed in the present disclosure, a binding structure under a condition where the second substance is constrained such that a binding state of the second substance to the first substance may be maintained in a predetermined state, is obtained. Then, based on this binding structure, a binding structure under a condition where the second substance is not constrained, is obtained.

The inventor of the technology disclosed in the present disclosure has examined a cause for reduction in calculation accuracy of the binding free energy when the binding state between substances easily changes.

When IT drug discovery such as "de novo" drug design is performed by molecular simulation using a computer, it is important to predict binding free energy indicating a binding activity value (dissociation constant) between a target molecule and a candidate molecule with high accuracy. In calculating the binding free energy between the target molecule and the candidate molecule, for example, highly accurate prediction such that an error is within 1.4 kcal/mol from an actual value (experimental value) is required.

Figure 1:
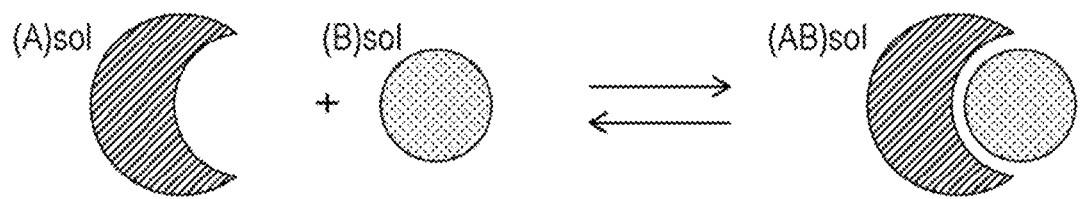
FIG. 1 is a diagram illustrating an example of a state of target molecules and candidate molecules in solution.

FIG. 1 is a diagram illustrating an example of a state of target molecules and candidate molecules in solution. In the state illustrated in FIG. 1, the target molecules A and the candidate molecules B that are bound to each other, and the target molecules A and the candidate molecules B that are not bound, are in an equilibrium state in the solution. In this case, a dissociation constant $K_d$ is represented by the following equation, where [A] is concentration of the target molecules A, [B] is concentration of the candidate molecules B, and [AB] is concentration of conjugates (complexes) of the target molecules A and the candidate molecules B in the solution. In the following equation, eq means that the concentration of the solution is in the equilibrium state.

$$K_d = \left[\frac{[A][B]}{[AB]}\right]_{eq}$$

Binding free energy ($\Delta G^\circ_{bind}$) to be determined by molecular simulation using a computer has a relation, which is expressed by the following equation, with the dissociation constant $K_d$ described above. $k_B$ represents the Boltzmann constant, T represents a temperature (K), and $C^\circ$ represents a standard concentration (1 mol/L).

$$\Delta G^\circ_{bind} = k_B T \ln\left[\frac{1}{C^\circ} \cdot K_d\right]$$

As illustrated in the above equation, when the dissociation constant $K_d$ as an experimental value and the calculated binding free energy $\Delta G^\circ_{bind}$ are compared, since the standard concentration $C^\circ$ is taken into consideration, it is preferable to control the concentration in the molecular simulation at a fixed level when calculating the binding free energy. The concentration in the molecular simulation means a spatial volume (space to be sampled) of sampling which is a process for acquiring data for calculating the binding free energy in the binding free energy calculation. In the binding free energy calculation, it is preferred to constrain (restrain) the candidate molecule to the target molecule to keep the spatial volume of the sampling fixed and to define the binding state between the target molecule and the candidate molecule.

Examples of a method for predicting the binding free energy between the target molecule and the candidate molecule by using the molecular simulation include an alchemical pathway calculation method, an umbrella sampling method, an extended ensemble method, and the like. Among these methods, it is known that the alchemical pathway calculation method is a method in which calculation accuracy of the binding free energy is high.

The alchemical pathway calculation method is also referred to as an alchemical free energy calculation method, an alchemical transformation method, or the like. The alchemical pathway calculation method uses a thermodynamic cycle along a virtual (alchemical) pathway to calculate the binding free energy. Specifically, for example, in the alchemical pathway calculation method, a constraint state of the candidate molecule to the target molecule on a distance or direction, and an interaction state between the candidate molecule and its surrounding molecules are controlled, and a change in free energy in each state is calculated. By doing so, in the alchemical pathway calculation method, a difference between free energy in a state in which the target molecule and the candidate molecule are not bound to each other and free energy in a state in which the target molecule and the candidate molecule are bound to each other may be accurately calculated. Thus, the binding free energy may be accurately obtained. Details of the alchemical pathway calculation method are described in, for example, E. Gallicchio, et al., "Recent Theoretical and Computational Advances for Modeling Protein-Ligand Binding Affinities", BioMaPS Institute for Quantitative Biology and Department of Chemistry and Chemical Biology, Rutgers Univ., Feb. 17, 2011, or the like.

Figure 2:
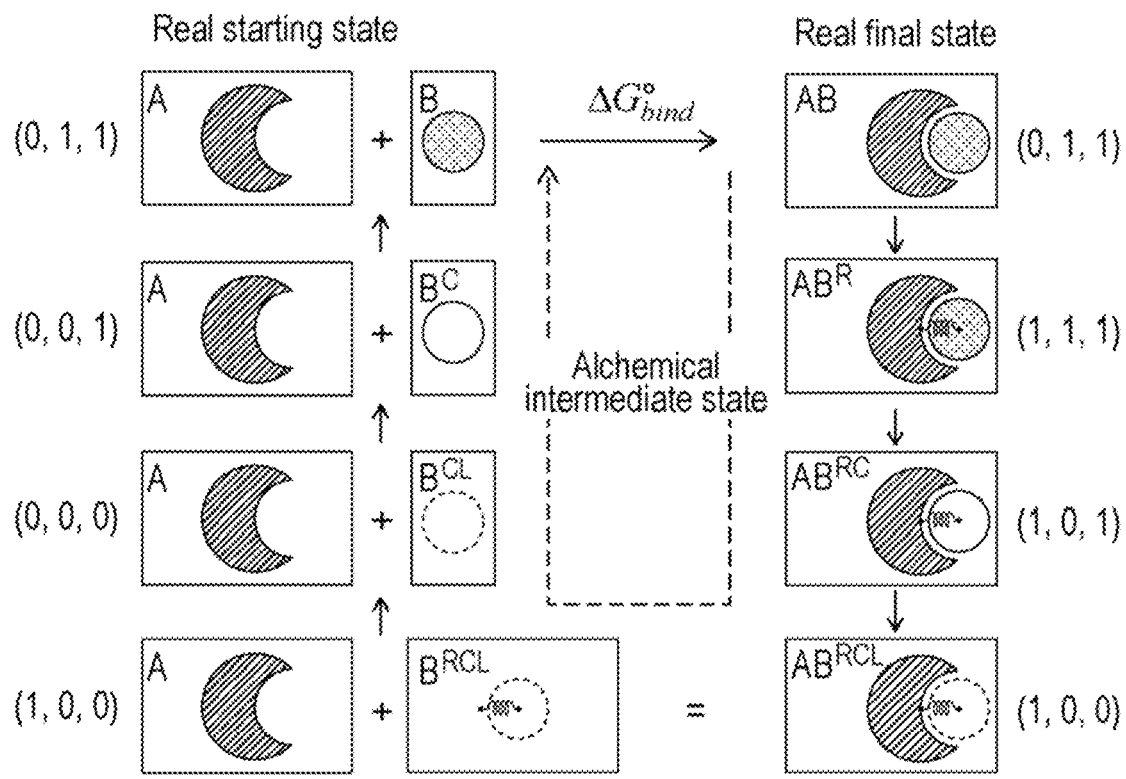
FIG. 2 is a diagram illustrating an example of a thermodynamic cycle in an alchemical pathway calculation method.

In the alchemical pathway calculation method, for example, the binding free energy is calculated based on a thermodynamic cycle illustrated in FIG. 2 and the following equation.

$$\Delta G_{bind}{}^\circ = \{\Delta G(B \rightarrow B^{\overline{C}}) + \Delta G(B^{\overline{C}} \rightarrow B^{\overline{CL}})\}$$

$$-\{\Delta G(AB^R \rightarrow AB^{R\overline{C}}) + \Delta G(AB^{R\overline{C}} \rightarrow AB^{R\overline{CL}})\}$$

$$-\Delta G(B^{R\overline{CL}} \rightarrow B^{\overline{CL}}) - \Delta G(AB \rightarrow AB^R)$$

FIG. 2 is a diagram illustrating an example of the thermodynamic cycle in the alchemical pathway calculation method. In FIG. 2, a crescent shaped object is the target molecule (A), and a circular object is the candidate molecule (B). In FIG. 2 and the above equation, C represents electrostatic interaction, L represents Van der Waals interaction, and R represents constraint on the candidate molecule.

The first, second, third, fourth, and sixth terms on the right side in the above equation may be obtained by, for example, a free energy perturbation (FEP) method, the Bennett acceptance ratio (BAR) method, the multi-state Bennett acceptance ratio (MBAR) method, a thermodynamic integration (TI) method, or the like. The second term from the last (fifth term) on the right side of the above equation may be referred to as standard state correction. Details of the standard state correction are described, for example, in Michael S. Lee et. al., "Calculation of Absolute Protein-Ligand Binding Affinity Using Path and Endpoint Approaches", Biophysical Journal, Volume 90, p. 864-877, February 2006 or the like.

In the binding free energy calculation using the alchemical pathway calculation method, a thermal equilibrium state (thermal equilibrium structure) in each state of processes (decoupling steps) of excluding the electrostatic interaction, the Van der Waals interaction, the constraint on the candidate molecule, and the like is obtained. This is because of a theoretical requirement that the thermal equilibrium structure in each state be used as an initial structure in sampling in the binding free energy calculation using the alchemical pathway calculation method. When parameters specifying respective states of the thermodynamic cycle in FIG. 2 are represented by $\lambda$, as denoted in the following equation, for example, the process of excluding the constraint on the candidate molecule corresponds to a process of shifting from a state of (0, 1, 1) to a state of (1, 1, 1) in FIG. 2.

$$\vec{\lambda} = (\lambda^R, \lambda^C, \lambda^{LJ})$$

In the above equation, $\lambda^R$ represents a parameter specifying a state of the constraint on the candidate molecule, $\lambda^C$ represents a parameter specifying a state of the electrostatic interaction, and $\lambda^{LJ}$ represents a parameter specifying a state of the Van der Waals interaction. Each parameter means a state in which there is no constraint on the candidate molecule, electrostatic interaction, or Van der Waals interaction when the parameter is "0", and means that the constraint on the candidate molecule, electrostatic interaction, or Van der Waals interaction is (fully) present when the parameter is "1".

However, when the thermal equilibrium state is obtained at each $\lambda$ of the decoupling step, a convergence speed to the thermal equilibrium state is significantly reduced, and time for calculation for obtaining the thermal equilibrium state (thermal equilibrium calculation) may be significantly increased. Therefore, when the thermal equilibrium state is obtained at each A in the decoupling step, there may be a case where preprocessing calculation is performed in order to increase the convergence speed to the thermal equilibrium state.

The preprocessing calculation (hereinafter also referred to simply as "preprocessing") may be performed by, for example, changing $\lambda$ between respective $\lambda_S$ stepwise (dividing into a plurality of states between respective $\lambda_S$). Changing $\lambda$ stepwise means that, for example, as illustrated in FIG. 2, when the state of (0, 1, 1) shifts to the state of (1, 1, 1), $\lambda^R$ is changed stepwise by finely dividing the state between $\lambda^S$, for example, into 0, 0.2, 0.4, 0.6, 0.8, and 1. When $\lambda$ is changed stepwise as described above, the convergence speed to the thermal equilibrium state may be made faster by continuously performing the short thermal equilibrium calculation at each $\lambda$. Continuously performing the short thermal equilibration calculation at each $\lambda$ means that, for example, after performing the short thermal equilibration calculation in the state where $\lambda^R$ is 0, a final structure in the short thermal equilibration calculation is set as the initial structure of the thermal equilibrium calculation in the state where $\lambda^R$ is 0.2.

Figure 3:
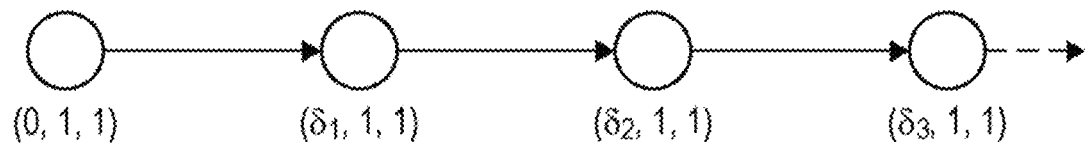
FIG. 3 is a diagram illustrating an example of a process of a preprocessing method of binding free energy calculation.

The preprocessing performed by changing $\lambda$ stepwise will be described in more detail with reference to a case where $\lambda^R$ is changed to 0, $\delta_1$, $\delta_2$, and $\delta_3$ as an example, as illustrated in FIG. 3. For example, the preprocessing in a state of ($\delta_1$, 1, 1) is carried out with the structure obtained by the preprocessing in the state of (0, 1, 1) (the final structure of the thermal equilibrium calculation in the state of (0, 1, 1)) set as an initial structure. By doing so, since an appropriate structure in each state may be set as the initial structure of the preprocessing, it is possible to shorten the time required for the preprocessing (thermal equilibrium calculation) in each state.

However, there is a problem that when the preprocessing that changes $\lambda$ stepwise as described above is performed, the calculation accuracy of the binding free energy is deteriorated when the binding state of the substances easily changes. More specifically, for example, when the preprocessing is performed by changing $\lambda$ stepwise from the state of (0, 1, 1) to the state of (1, 1, 1) in FIG. 2, the calculation accuracy of the binding free energy may decrease when an energy barrier separating each binding state of the candidate molecule is low.

The above problem will be described in more detail.

Figure 4:
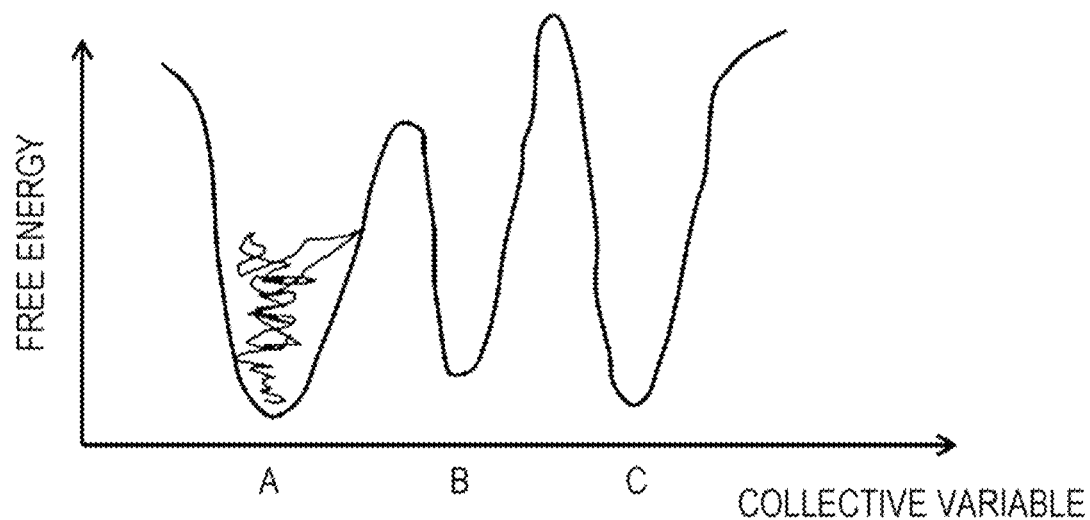
FIG. 4 is a diagram illustrating an example of a free energy curve.

When the preprocessing of the binding free energy calculation is performed by changing $\lambda$ stepwise along a pathway in FIG. 2, the preprocessing calculation is performed in which the constraint on the candidate molecule is very weak in a state ($\epsilon$, 1, 1) in a vicinity of (0, 1, 1) between the state of (0, 1, 1) and the state of (1, 1, 1). When a free energy curve related to a complex structure of the target molecule and the candidate molecule is shaped as illustrated in FIG. 4, the complex structure is separated by an energy barrier that is sufficiently larger than room temperature fluctuation $k_B T$ ($k_B$: Boltzmann constant, T: temperature). Therefore, when the free energy curve is shaped as illustrated in FIG. 4, it is assumed that the complex structure remains in a state of an original structure A even when the preprocessing calculation is performed in which the constraint on the candidate molecule is very weak in the state of ($\epsilon$, 1, 1) in the vicinity of (0, 1, 1) in FIG. 2. In addition, each of collective variables in FIG. 4 and FIG. 5 is sometimes referred to as reaction coordinates, and means a geometric parameter that changes during a shift of the state of the complex structure (binding state).

Figure 5:
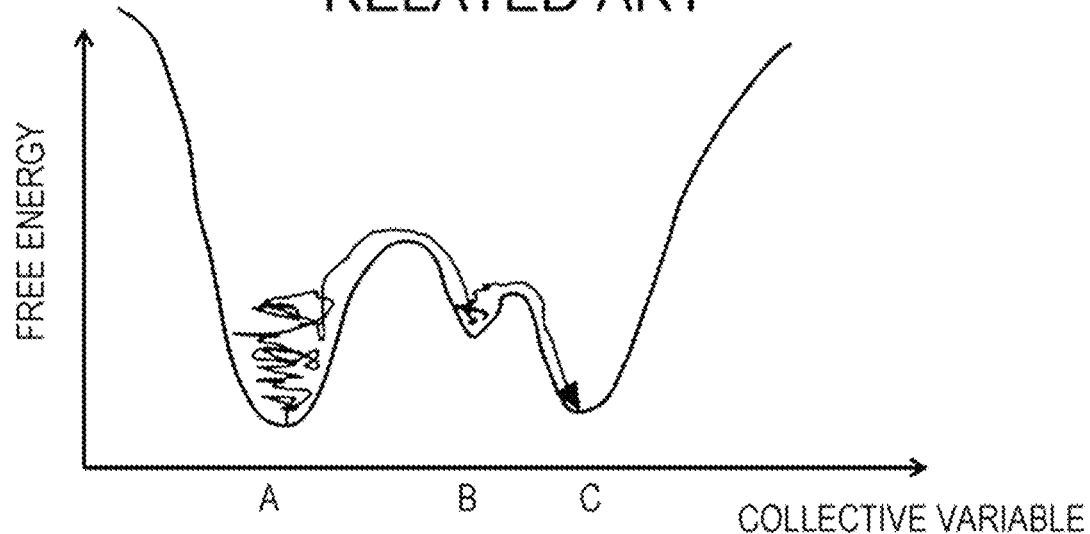
FIG. 5 is a diagram illustrating another example of the free energy curve.

On the other hand, in a case where the free energy curve related to the complex structure is shaped as illustrated in FIG. 5, when the preprocessing calculation is performed in which the constraint on the candidate molecule is very weak in the vicinity of (0, 1, 1) in FIG. 2, the complex structure may shift to a state of a structure B or a structure C different from the state of the original structure A. Consequently, although the initial structure of the binding free energy calculation in the state of the structure A is required to be obtained in the preprocessing, in actuality, the state of the structure B or the structure C may be obtained as the initial structure by exceeding the energy barrier due to the room temperature fluctuation. Therefore, in the preprocessing method described above, the binding state between the target molecule and the candidate molecule shifts in the preprocessing, whereby the spatial volume of the sampling in the binding free energy calculation is changed, so that it may be difficult to quantitatively predict the binding free energy.

The inventor of the technology disclosed in the present disclosure has found that the above problem may be solved by obtaining the binding structure under a condition where the candidate molecule is not constrained, based on the binding structure (complex structure) under a condition where the binding state of the candidate molecule to the target molecule is maintained in a predetermined state. An example of the technology disclosed in the present disclosure will be described with reference to FIG. 6 and FIG. 7.

Figure 6:
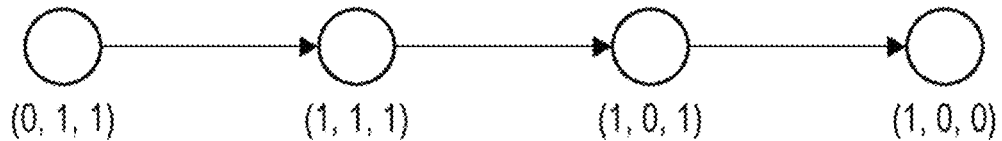
FIG. 6 is a diagram illustrating another example of the process of the preprocessing method of the binding free energy calculation.
Figure 7:
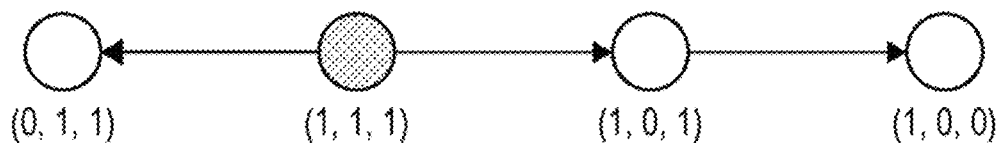
FIG. 7 is a diagram illustrating an example of a process of a preprocessing method of binding free energy calculation disclosed in the present disclosure.

As illustrated in FIG. 6, when the preprocessing is performed by changing λ stepwise from the state of (0, 1, 1) to the state of (1, 1, 1), the state of the complex structure may shift when the preprocessing calculation is performed in which the constraint in the state of (ε, 1, 1) in the vicinity of (0, 1, 1) is very weak. On the other hand, in an example of the technology disclosed in the present disclosure, for example, as illustrated in FIG. 7, λ is changed stepwise from the state of (1, 1, 1) to the state of (0, 1, 1) to perform preprocessing. Thus, in the technology disclosed in the present disclosure, the binding structure under a condition where the candidate molecule is constrained is obtained, and based on the obtained binding structure, the binding structure is obtained under the condition where the candidate molecule is not constrained. In this way, in the technology disclosed in the present disclosure, in one aspect, it is possible to suppress a change in the spatial volume of the sampling in the binding free energy calculation because of the shift of the binding state between the target molecule and the candidate molecule in the preprocessing. Therefore, in one aspect, the technology disclosed in the present disclosure may improve the calculation accuracy of the binding free energy even when the binding state between the substances easily changes. This is considered to be because it is possible to suppress the shift of the binding state between the target molecule and the candidate molecule in a case of excluding the constraint from the state where the candidate molecule is constrained rather than in a case of constraining the candidate molecule from the state where the candidate molecule is not constrained.

Figure 8:
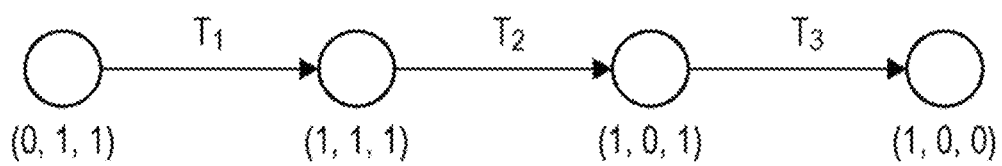
FIG. 8 is a diagram illustrating an example of the process of the preprocessing method of the binding free energy calculation and time required for the preprocessing.

In the technology disclosed in the present disclosure, in one aspect, when using a computer capable of performing parallel processing, it is possible to shorten the calculation time required for the preprocessing. It will be described, with reference to FIG. 8 and FIG. 9, that the technology disclosed in the present disclosure may shorten the calculation time required for the preprocessing. First, as illustrated in FIG. 8, a case is considered where the preprocessing is started from the state of (0, 1, 1), λ is changed stepwise, and the state of (1, 1, 1), a state of (1, 0, 1), and a state of (1, 0, 0) are sequentially preprocessed. In this case, the preprocessing in each state is performed sequentially from preprocessing in the state of (0, 1, 1) since the preprocessing is performed using the final structure in the previous state.

As in the example illustrated in FIG. 8, it is assumed that total calculation time required for the preprocessing for a shift from the state of (0, 1, 1) to the state of (1, 1, 1) is $T_1$. Similarly, it is assumed that total calculation time required for the preprocessing for a shift from the state of (1, 1, 1) to the state of (1, 0, 1) is $T_2$, and that total calculation time required for the preprocessing for a shift from the state of (1, 0, 1) to the state of (1, 0, 0) is $T_3$. In this case, time required for the entire preprocessing from the state of (0, 1, 1) to the state of (1, 0, 0) is $T_1+T_2+T_3$.

Figure 9:
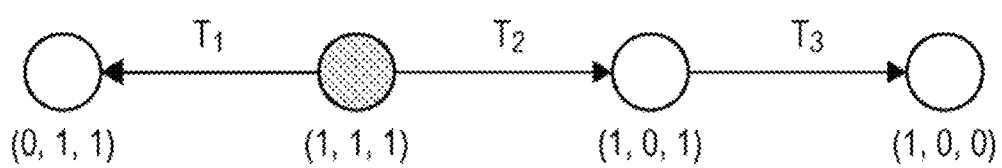
FIG. 9 is a diagram illustrating an example of the process of the preprocessing method of the binding free energy calculation disclosed in the present disclosure and the time required for the preprocessing.

On the other hand, in an example of the technology disclosed in the present disclosure, the preprocessing is started from the state of (1, 1, 1) as illustrated in FIG. 9, for example. In this way, the preprocessing for the shift from the state of (1, 1, 1) to the state of (0, 1, 1) and the preprocessing for the shift from the state of (1, 1, 1) to the state of (1, 0, 1) are independent from each other (that is, for example, each preprocessing does not require a result of the other preprocessing). For this reason, the preprocessing for the shift from the state of (1, 1, 1) to the state of (0, 1, 1) and the preprocessing for the shift from the state of (1, 1, 1) to the state of (1, 0, 1) may be processed in parallel. For example, as in the example illustrated in FIG. 9, it is assumed that total calculation time required for each preprocessing when shifting to each state in the same manner as in the case of FIG. 8 is defined as $T_1$, $T_2$, and $T_3$. In this case, it is possible to perform the preprocessing requiring time $T_1$ and the preprocessing requiring time $T_2$ in parallel, so that the time required for the entire preprocessing from the state of (0, 1, 1) to the state of (1, 0, 0) is the longer one of $T_1$ and $T_2+T_3$.

In this manner, in the technology disclosed in the present disclosure, in one aspect, when using a computer capable of performing parallel processing, it is possible to shorten the calculation time required for the preprocessing. Thus, an example of the technology disclosed in the present disclosure may shorten the calculation time required for the preprocessing by parallel performing a plurality of calculations for obtaining the binding structure of the target molecule and the candidate molecule under conditions where the parameters (λ) specifying the state of the candidate molecule are different from each other.

The preprocessing method of binding free energy calculation disclosed in the present disclosure may be particularly suitably used when the binding free energy calculation is performed by the alchemical pathway calculation method. The technology disclosed in the present disclosure is not limited to be applied to the target molecule and the candidate molecule, and is applicable to a combination of the first substance and the second substance capable of forming a complex.

<Calculation of Binding Structure Under Condition Where Second Substance Is Constrained>

First, in an example of the technology disclosed in the present disclosure, the binding structure of the first substance and the second substance is obtained under the condition where the second substance is constrained such that it is possible to maintain the binding state of the second substance to the first substance in a predetermined state.

The combination of the first substance and the second substance is not particularly limited as long as it is a combination capable of forming a complex, and may be appropriately selected according to the purpose. The complex is formed, for example, by various kinds of interaction.

Examples of the first substance include the target molecule and the like. Examples of the second substance include the candidate molecule whose binding property to the target molecule is evaluated and the like.

The target molecule is not particularly limited and may be appropriately selected depending on the purpose, and examples thereof include protein, ribonucleic acid (RNA), deoxyribonucleic acid (DNA), and the like. The candidate molecule is not particularly limited and may be appropriately selected depending on the purpose, and examples thereof include a molecule which becomes a drug candidate (drug candidate molecule), a fragment which is used when a drug candidate molecule is designed, or the like. The fragment is used, for example, in fragment-based drug design (FBDD).

The first substance may be, for example, an antibody, DNA or the like, and the second substance may be, for example, a pathogen, a cancer cell, a stress substance, or the like. These first substances may be used, for example, in detecting these second substances. The technology disclosed in the present disclosure may, in one aspect, be used in evaluating capability of the first substance to detect the second substance.

Constraining the second substance such that the binding state of the second substance to the first substance is maintained in a predetermined state means constraining the second substance such that the binding state of the second substance does not shift when the binding structure under the condition where the second substance is constrained is obtained. Thus, constraining the second substance such that the binding state is maintained in the predetermined state means constraining the second substance such that the binding structure does not shift from a desired state (a desired energy valley) during the calculation (simulation) under the condition where the second substance is constrained.

A method of constraining the second substance such that the binding state of the second substance to the first substance is maintained in the predetermined state is not particularly limited, and may be appropriately selected according to the purpose, but a method in which a constraint potential is added to the second substance is preferable. The constraint potential is not particularly limited as long as it is a potential capable of at least constraining the second substance, and may be appropriately selected depending on the purpose, and examples thereof include a harmonic potential, a well-type potential, and the like.

The harmonic potential is a constraint potential that constrains by using a force proportional to a distance from a fixed point, and is also referred to as the constraint potential by a spring. In the technology disclosed in the present disclosure, it is preferable that the constraint potential be the harmonic potential since constraint strength of the second substance may be set as appropriate. Addition of the harmonic potential may be performed, for example, by adding the harmonic potential gradually from zero to a maximum value, or by adding the harmonic potential having a predetermined strength from the beginning of calculation. A spring constant $K_\xi$ that defines a strength (magnitude) of the harmonic potential may be appropriately selected depending on the combination of the first substance and the second substance within a range in which the binding structure may be maintained in a desired state. The spring constant $K_\xi$ is preferably set to a sufficiently large value to ensure that the binding state of the second substance to the first substance is maintained in a predetermined state.

The constraint potential is applied between the first substance and the second substance, for example, by using an anchor point of the first substance and an anchor point of the second substance. The constraint potential to be applied between the anchor point of the first substance and the anchor point of the second substance is determined, for example, such that size of fluctuation of the second substance falls within a specific range.

The distance constraint between the first substance and the second substance is carried out, for example, in order to correctly take into account the degree of freedom in translation of a molecule which has the greatest contribution to the binding activity. Therefore, it is preferable that a center of gravity of the second substance be set to be an anchor point of the second substance. The center of gravity of the second substance may be obtained by, for example, the following equation.

$$\vec{x}_{com} = \frac{\sum m_i \vec{x}_i}{\sum m_i}$$

In the above equation, m represents mass and x represents coordinates of atom forming the second substance. Since a hydrogen atom is light, influence on a position of a center of gravity is small. Therefore, it is preferable that the center of gravity of the second substance be obtained by removing hydrogen atoms forming the second substance from the viewpoint of shortening the calculation time. Hereinafter, atoms except for a hydrogen atom are sometimes referred to as heavy atoms.

A method for obtaining the binding structure (complex structure) of the first substance and the second substance is not particularly limited and may be appropriately selected depending on the purpose, and examples thereof include the molecular mechanics method, the molecular dynamics method, and the like. Among these methods, the molecular dynamics method is preferable as a method for obtaining the binding structure of the first substance and the second substance. The molecular dynamics (MD) method means a method for simulating motion of particles (mass points) such as atoms by numerically solving the Newtonian equation of motion. Molecular dynamics calculation (simulation) by the molecular dynamics method may be performed by using, for example, a molecular dynamics calculation program. Examples of the molecular dynamics calculation program include, for example, AMBER, CHARMm, GROMACS, GROMOS, NAMD, myPresto, MAPLECAFEE (registered trademark), and the like.

In the molecular dynamics calculation, for example, it is possible to relax the binding structure to a thermal equilibrium state (a state close to the thermal equilibrium state) by, for example, performing the calculation under a fixed temperature and pressure condition (NPT ensemble) or the like. Consequently, in the technology disclosed in the present disclosure, in one aspect, by obtaining the binding structure of the first substance and the second substance by the molecular dynamics calculation, the binding structure which is considered to be in the thermal equilibrium state may be obtained.

A method for preparing the initial structure for obtaining the binding structure (complex structure) of the first substance and the second substance is not particularly limited, and may be appropriately selected depending on the purpose. The initial structure for obtaining the binding structure of the first substance and the second substance may be prepared, for example, by using a function of the molecular dynamics calculation program described above based on three-dimensional structure data of the first substance and the second substance or the like. The three-dimensional data of the first substance and the second substance may be prepared from experimental data obtained from, for example, X-ray crystal structure analysis, nuclear magnetic resonance (NMR) analysis, analysis using a cryo-electron microscope, or the like. The three-dimensional structure data prepared by these methods may be obtained, for example, from a RCSB protein data bank (PDB), or the like. For example, the initial structure of the first substance (for example, protein as the target molecule or the like) may be prepared from the three-dimensional structure data based on the experimental data described above, and the initial structure of the second substance (for example, the candidate molecule) may be prepared by designing with modeling software or the like. As the initial structure of the first substance (for example, protein as the target molecule or the like), for example, a three-dimensional structure predicted by a technique such as homology modeling, a three-dimensional structure complemented by modeling a deleted portion (deleted residue) in the three-dimensional structure data obtained from the RCSB PDB, or the like may be used. It is preferable to use a structure in which water molecules are arranged around the binding structure of the first substance and the second substance, for the initial structure for obtaining the binding structure of the first substance and the second substance.

<Calculation of Binding Structure Under Condition Where Second Substance Is Not Constrained>

Next, in an example of the technology disclosed in the present disclosure, based on the binding structure under the condition where the second substance is constrained, obtained as described above, the binding structure under the condition where the second substance is not constrained is obtained. Thus, in an example of the technology disclosed in the present disclosure, the binding structure under the condition where the second substance is not constrained is obtained by setting the binding structure under the condition where the second substance is constrained as the initial structure.

When the binding structure under the condition where the second substance is not constrained is obtained based on the binding structure under the condition where the second substance is constrained, it is preferable to obtain the binding structure under the condition where the second substance is not constrained by weakening stepwise the constraint on the second substance. The constraint on the second substance may be weakened stepwise by, for example, adding the harmonic potential while gradually decreasing from a maximum value to zero or the like. In the technology disclosed in the present disclosure, in one aspect, by weakening stepwise the constraint on the second substance, the binding structure under the condition where the second substance is not constrained is obtained. Thus, it is possible to more reliably suppress the shift of the binding state of the first substance and the second substance in the preprocessing. Accordingly, in the technology disclosed in the present disclosure, in one aspect, even when the binding state between substances easily changes, the calculation accuracy of the binding free energy may be more reliably improved.

When the binding free energy calculation is performed by the above described alchemical pathway calculation method, the parameter (for example, λ described above) specifying a state of the second substance may be changed stepwise along a pathway of a thermodynamic cycle in the alchemical pathway calculation method. In this calculation, cases are considered where the binding structures under a condition where the parameter is a first numerical value and under a condition where the parameter is a second numerical value that is a numerical value next to the first numerical value are obtained. In this case, in an example of the technology disclosed in the present disclosure, it is preferable to obtain the binding structure under the condition where the parameter is the first numerical value, and to obtain the binding structure under the condition where the parameter is the second numerical value based on the obtained binding structure under the condition where the parameter is the first numerical value. Thus, in an example of the technology disclosed in the present disclosure, it is preferable that the structure (final structure) as a result of performing the preprocessing under the condition where the parameter is the first numerical value be set as the initial structure of the preprocessing under the condition where the parameter is the second numerical value. In this way, the technology disclosed in the present disclosure may, in one aspect, since an appropriate structure in each state may be used as the initial structure for the preprocessing, it is possible to shorten time required for the preprocessing in each state.

When the binding structure under the condition where the second substance is not constrained is obtained, it is possible to calculate the constraint on the second structure and the binding structure by, for example, using the same method as that used in obtaining the binding structure under the condition where the second substance is constrained.

The preprocessing method of the binding free energy calculation disclosed in the present disclosure may be implemented by using a normal computer system provided with, for example, a CPU, a RAM, a hard disk, any of various peripheral devices, and the like. The CPU refers to a central processing unit, and the RAM refers to a random-access memory. Examples of the normal computer system provided with the any of various peripheral devices and the like, for example, include a computer system having any of various network servers, workstations, personal computers, and the like.

Figure 10:
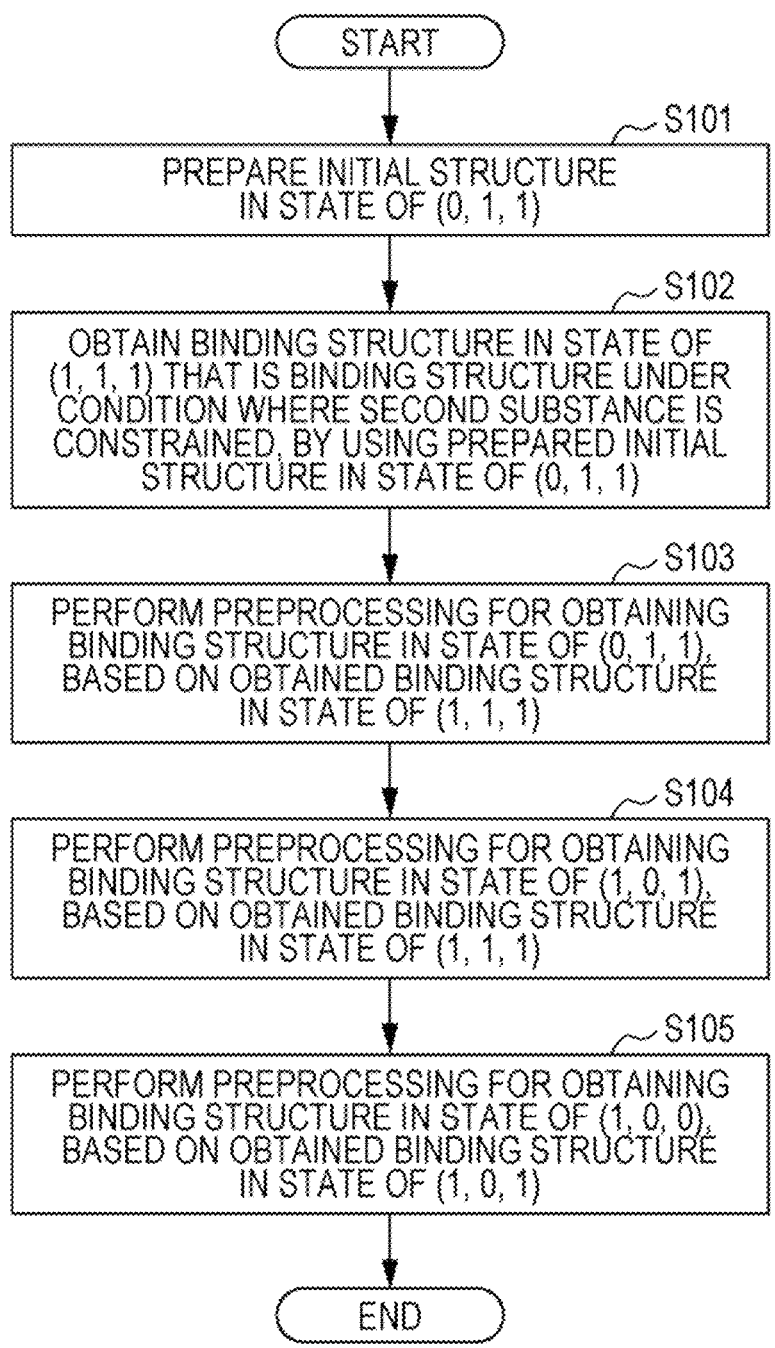
FIG. 10 is a flowchart of an example of the preprocessing method of the binding free energy calculation disclosed in the present disclosure.

An example of the preprocessing method of the binding free energy calculation disclosed in the present disclosure will now be described with reference to a flowchart. FIG. 10 illustrates an example of a procedure in a case where the preprocessing is sequentially performed (without performing parallel processing).

First, in step S101, the initial structures of the first substance and the second substance corresponding to the state of (0, 1, 1) in FIG. 2 are prepared.

Next, in step S102, by using the initial structures in the state of (0, 1, 1) that have been prepared in step S101, the binding structure in the state of (1, 1, 1) which is the binding structure under the condition where the second substance is constrained, is obtained.

Next, in step S103, the preprocessing for obtaining the binding structure in the state of (0, 1, 1) is performed based on the binding structure in the state of (1, 1, 1) that has been obtained in step S102.

Next, in step S104, the preprocessing for obtaining the binding structure of the state of (1, 0, 1) is performed based on the binding structure in the state of (1, 1, 1) that has been obtained in step S102.

Next, in step S105, the preprocessing for obtaining the binding structure of the state of (1, 0, 0) is performed based on the binding structure in the state of (1, 0, 1) that has been obtained in step S104.

In an example of the preprocessing procedure illustrated in FIG. 10, step S104 and S105 are performed after step S103 is performed, but the technology disclosed in the present disclosure is not limited to this, and for example, step S103 may be performed after step S104 and step S105 are performed.

Figure 11:
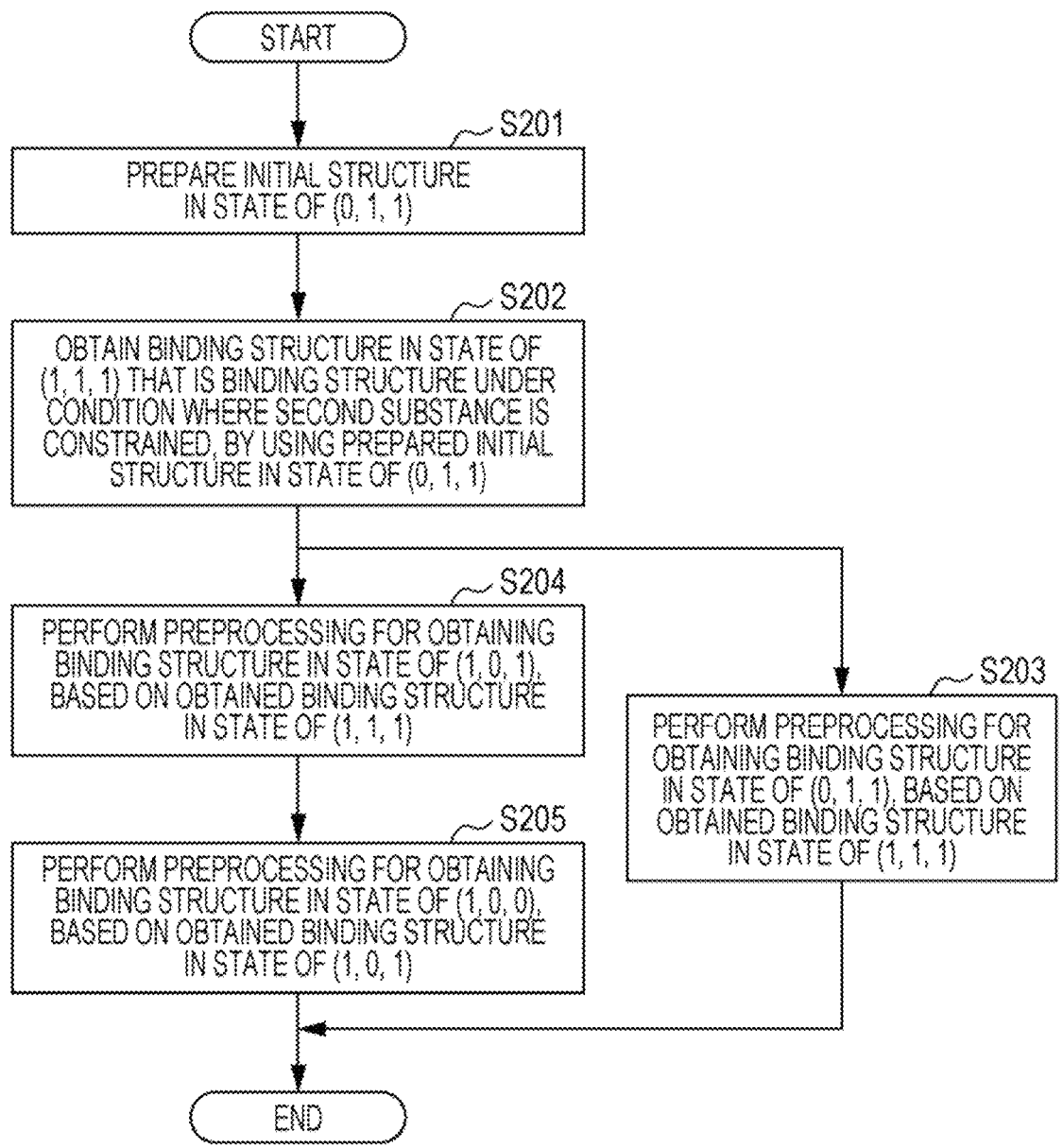
FIG. 11 is a flowchart of another example of the preprocessing method of the binding free energy calculation disclosed in the present disclosure.

FIG. 11 illustrates an example of a procedure in a case where a plurality of pieces of preprocessing are executed in parallel by using a computer capable of performing parallel processing.

Step S201 to step S205 in FIG. 11 correspond to step S101 to step S105 in FIG. 10, respectively.

In the example illustrated in FIG. 11, step S203 and steps S204 and S205 are simultaneously performed in parallel. In this way, in the example illustrated in FIG. 11, it is possible to shorten the calculation time required for the preprocessing.

(Binding Free Energy Calculation Method)

The binding free energy calculation method disclosed in the present disclosure is a binding free energy calculation method for calculating the binding free energy between the first substance and the second substance by using a computer. In the binding free energy calculation method disclosed in the present disclosure, calculation for calculating the binding free energy is performed after the preprocessing is performed in the preprocessing method of the binding free energy calculation disclosed in the present disclosure. By doing so, the binding free energy calculation method disclosed in the present disclosure may improve the calculation accuracy of the binding free energy even when the binding state between the substances easily changes, in one aspect.

The calculation for calculating the binding free energy is not particularly limited and may be appropriately selected depending on the purpose, but it is preferable to perform the calculation according to the alchemical pathway calculation method described above.

(Preprocessing Program for Binding Free Energy Calculation)

A preprocessing program for the binding free energy calculation is a program that causes a computer to execute the preprocessing for the binding free energy calculation disclosed in the present disclosure. The preprocessing program for the binding free energy calculation disclosed in the present disclosure may be prepared using any of various known program languages depending on a type, a version, and the like of a computer system and an operating system to be used.

The preprocessing program for the binding free energy calculation disclosed in the present disclosure may be recorded on a recording medium such as a built-in hard disk, or an external hard disk, or may be recorded on a recording medium such as a compact disc read-only memory (CD-ROM), a digital versatile disk read-only memory (DVD-ROM), a magneto-optical (MO) disk, or a Universal Serial Bus (USB) memory (USB flash drive).

When the preprocessing program for the binding free energy calculation disclosed in the present disclosure is to be recorded on the recording medium described above, it is possible to directly use the preprocessing program, or to use the preprocessing program by installing it on a hard disk, through a recording medium reading apparatus included in the computer system, as required. The preprocessing program for the binding free energy calculation disclosed in the present disclosure may be recorded in an external storage area (another computer or the like) accessible from the computer system through an information communication network. In this case, the preprocessing program for the binding free energy calculation disclosed in the present disclosure recorded in the external storage area may be directly used or be used by installing the preprocessing program on the hard disk from the external storage area through the information communication network, as required.

The preprocessing program for the binding free energy calculation disclosed in the present disclosure may be divided and recorded on a plurality of recording media for each arbitrary process.

(Computer Readable Recording Medium)

The computer readable recording medium disclosed in the present disclosure is configured to record the preprocessing program for the binding free energy calculation disclosed in the present disclosure. The computer readable recording medium disclosed in the present disclosure is not particularly limited, and may be appropriately selected depending on the purpose, and examples thereof include, for example, a built-in hard disk, an external hard disk, a CD-ROM, a DVD-ROM, an MO disk, a USB memory, and the like. The computer readable recording medium disclosed in the present disclosure may be a plurality of recording media in which the preprocessing program for the binding free energy calculation disclosed in the present disclosure is divided and recorded for each arbitrary process.

(Preprocessing Apparatus for Binding Free Energy Calculation)

The preprocessing apparatus for the binding free energy calculation disclosed in the present disclosure includes at least a control unit, and further includes other units as required. The preprocessing apparatus for the binding free energy calculation disclosed in the present disclosure obtains the binding structure of the first substance and the second substance that is the initial structure of the binding free energy calculation of the first substance and the second substance. The control unit in the preprocessing apparatus for the binding free energy calculation disclosed in the present disclosure obtains the binding structure under the condition where the second substance is constrained such that the binding state of the second substance to the first substance may be maintained in a predetermined state. Then, based on this binding structure, the binding structure under the condition where the second substance is not constrained, is obtained. The preprocessing method of the binding free energy calculation disclosed in the present disclosure may be applied to, for example, the preprocessing apparatus for the binding free energy calculation disclosed in the present disclosure.

Figure 12:
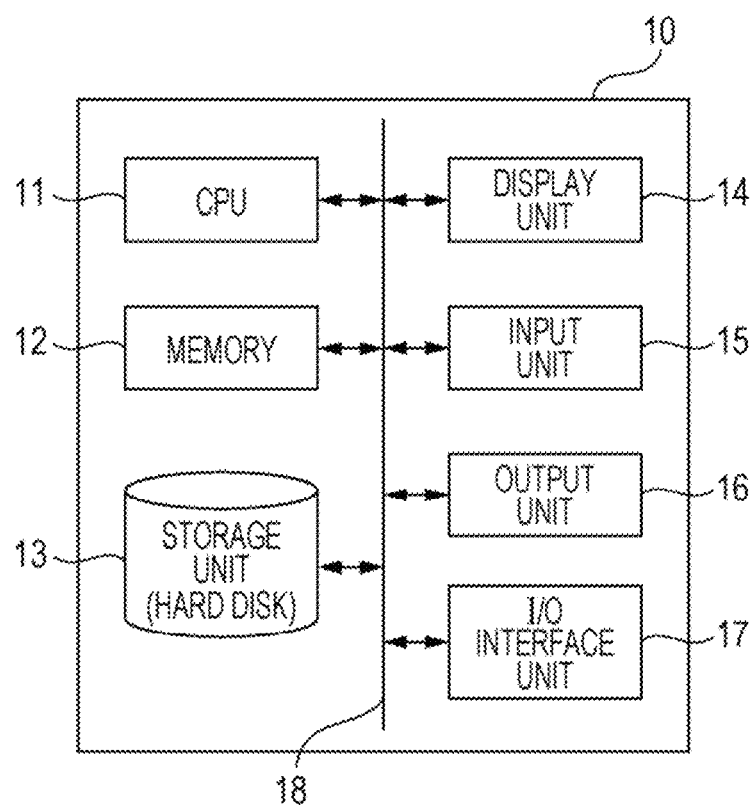
FIG. 12 is a diagram illustrating a configuration example of a preprocessing apparatus for binding free energy calculation disclosed in the present disclosure.

FIG. 12 illustrates a configuration example of the preprocessing apparatus for the binding free energy calculation disclosed in the present disclosure. In a preprocessing apparatus 10 for the binding free energy calculation, for example, a CPU 11 (control unit), a memory 12, a storage unit 13, a display unit 14, an input unit 15, an output unit 16, and an I/O interface unit 17 are coupled via a system bus 18.

The CPU 11 performs operations (four arithmetic operations, comparison operation, and the like), operation control of hardware and software, and the like. The memory 12 is a memory such as a RAM or a ROM. The RAM stores an operating system (OS), an application program, and the like read from the ROM and the storage unit 13, and functions as a main memory and a work area of the CPU 11. The storage unit 13 is a device for storing various programs and data, and is a hard disk, for example. The storage unit 13 stores a program to be executed by the CPU 11, data required for execution of the program, the OS, and the like. The preprocessing program for the binding free energy calculation disclosed in the present disclosure is stored in the storage unit 13, loaded into the RAM (main memory) of the memory 12, and executed by the CPU 11. The display unit 14 is a display device, and is, for example, a display device such as a CRT monitor, or a liquid crystal panel. The input unit 15 is an input device for various data, and is, for example, a keyboard, a pointing device (for example, a mouse, or the like), or the like. The output unit 16 is an output device for various data, and is, for example, a printer, or the like. The I/O interface unit 17 is an interface for coupling various external devices. The I/O interface unit 17 enables, for example, input and output of data such as a CD-ROM, a DVD-ROM, an MO disk, and a USB memory.

Figure 13:
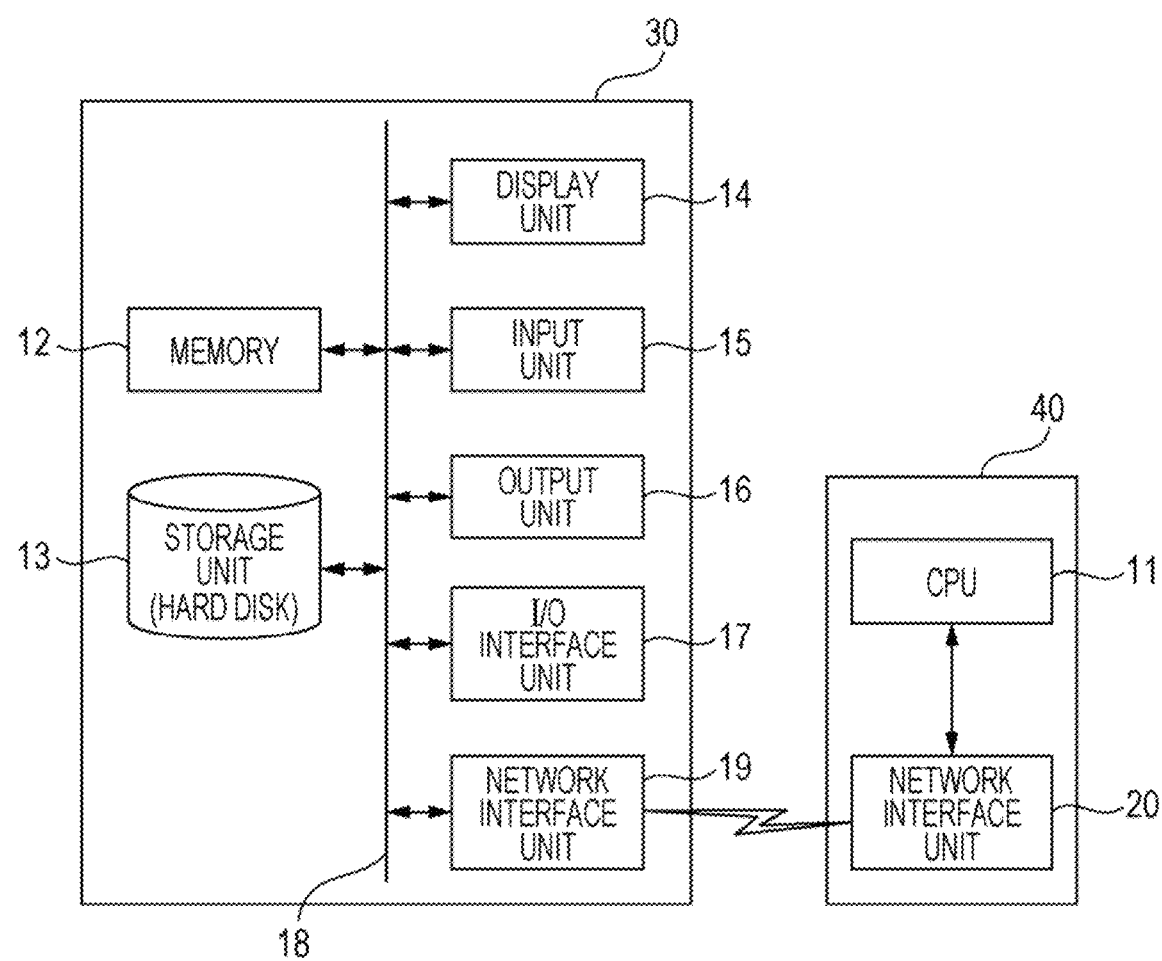
FIG. 13 is a diagram illustrating another configuration example of the preprocessing apparatus for the binding free energy calculation disclosed in the present disclosure.

FIG. 13 illustrates another configuration example of the preprocessing apparatus for the binding free energy calculation disclosed in the present disclosure. The example illustrated in FIG. 13 is an example in which the preprocessing apparatus for the binding free energy calculation is made to be a cloud type, and the CPU 11 is independent of the storage unit 13 and the like. In the example illustrated in FIG. 13, the computer 30 in which the storage unit 13 and the like are stored, and the computer 40 in which the CPU 11 is stored are coupled via network interface units 19 and 20. The network interface units 19 and 20 are hardware configured to perform communication by using the Internet.

Figure 14:
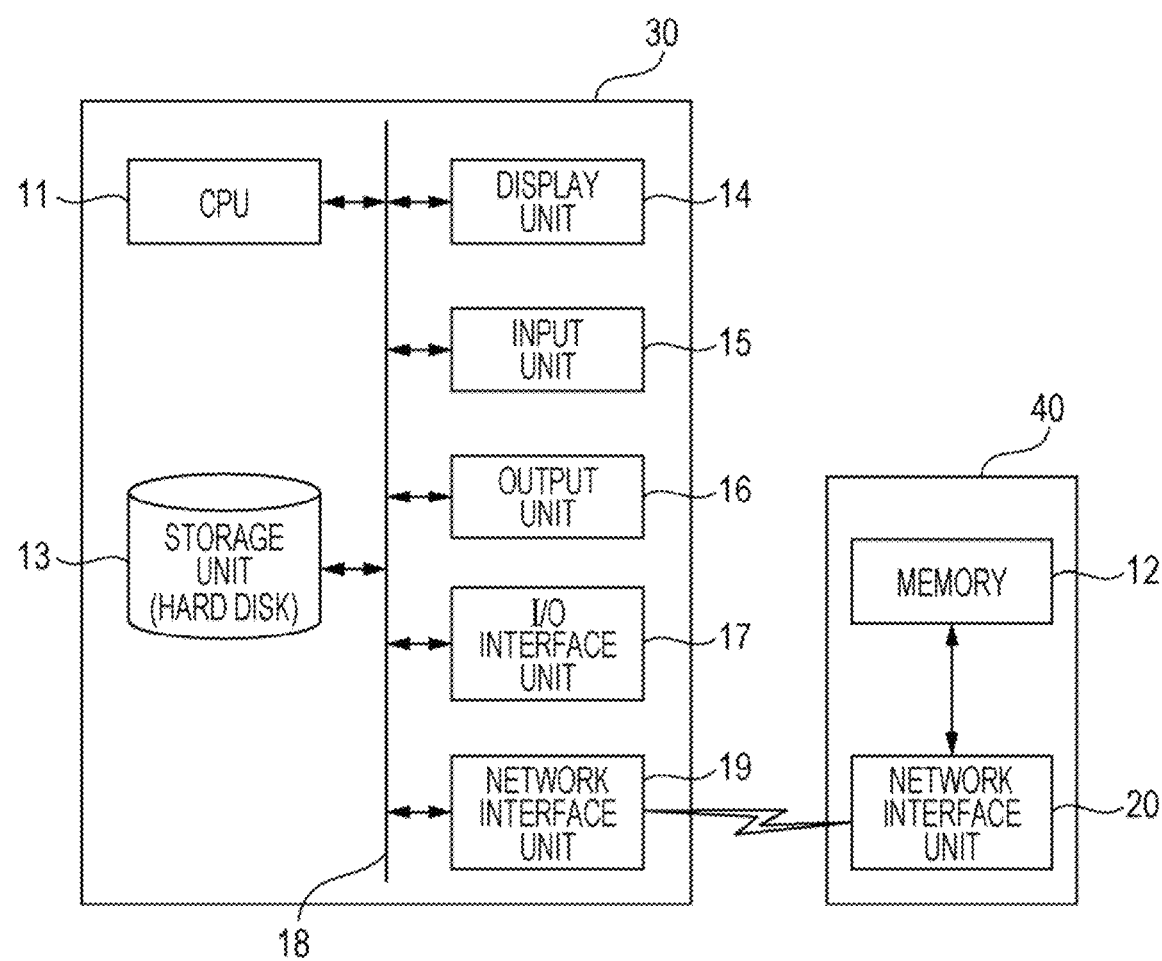
FIG. 14 is a diagram illustrating another configuration example of the preprocessing apparatus for the binding free energy calculation disclosed in the present disclosure.

FIG. 14 illustrates another configuration example of the preprocessing apparatus for the binding free energy calculation disclosed in the present disclosure. The example illustrated in FIG. 14 is an example in which the preprocessing apparatus for the binding free energy calculation is made to be a cloud type, and the storage unit 13 is independent of the CPU 11 and the like. In the example illustrated in FIG. 14, the computer 30 in which the CPU 11 and the like are stored, and the computer 40 in which the storage unit 13 is stored are coupled via the network interface units 19 and 20.

EXAMPLE

Hereinafter, the technology disclosed in the present disclosure will be described in more detail with reference to an example, but the technology disclosed in the present disclosure is not limited to the following example.

Example 1

For the system (PDB ID: 3KR8) of tankyrase 2 as the first substance and XAV-939 as the second substance, the binding free energy calculation was carried out by using the preprocessing method of the binding free energy calculation disclosed in the present disclosure. The procedure will be described.

Figure 15:
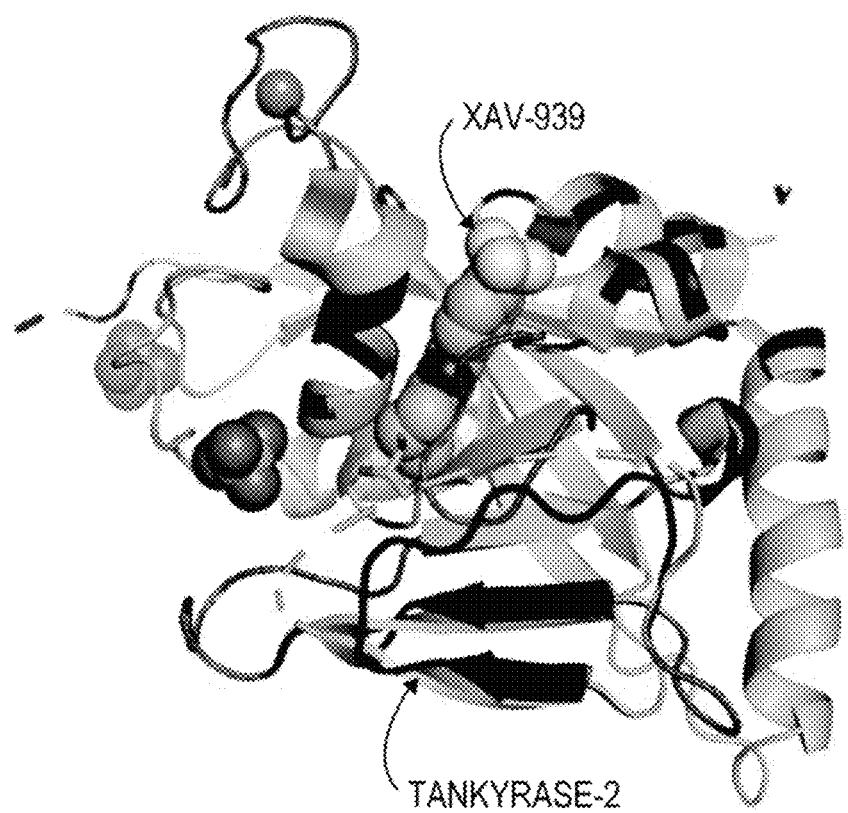
FIG. 15 is a diagram illustrating superimposition of a structure of PDB ID: 3KR8 on a structure of PDB ID: 3UH4, which is a complex structure of tankyrase 2 and XAV-939 in which a deleted residue is complemented in Example 1.

First, the deleted residue in PDB ID: 3KR8 describe above was complemented with reference to PDB ID: 3UH4 that is a three-dimensional structure of a complex of tankyrase 1 and XAV-939. FIG. 15 illustrates superimposition of a structure of 3KR8 on a structure of 3UH4, which is a complex structure of tankyrase 2 and XAV-939 in which the deleted residue is complemented.

Then, based on the complemented structure, an initial structure that may be used for molecular dynamics calculation was prepared. The initial structure which may be used for the molecular dynamics calculation may be prepared by, for example, adding hydrogen atoms to protein, arranging water molecules around protein, or the like.

By using the prepared initial structure, the molecular dynamics calculation was carried out under a condition where XAV-939 was constrained, thereby obtaining the binding structure of tankyrase 2 and XAV-939 that corresponded to the state of (1, 1, 1) illustrated in FIG. 2. As the constraint on XAV-939, a constraint having sufficient strength enough to avoid the shift of the binding state of XAV-939 was applied by using the harmonic potential.

Subsequently, by using the obtained binding structure, the constraint on XAV-939 was weakened stepwise ($\lambda$ was changed stepwise from 1 to 0) to obtain the binding structure (corresponding to the state of (0, 1, 1) in FIG. 2) under the condition where the XAV-939 was not constrained. When $\lambda$ was changed stepwise from 1 to 0, a structure (final structure) that was a result of the preprocessing under a first condition was used as an initial structure of the preprocessing under the following condition.

Next, the binding structure of tankyrase 2 and XAV-939 corresponding to the state of (1, 1, 1) in FIG. 2 was used to obtain the binding structure corresponding to the state of (1, 0, 1) in FIG. 2. Subsequently, the binding structure corresponding to the state of (1, 0, 0) was obtained by using the obtained binding structure corresponding to the state of (1, 0, 1) illustrated in FIG. 2, and the preprocessing for the binding free energy calculation was performed. In these pieces of calculation, when $\lambda$ was changed stepwise from 1 to 0, the structure (final structure) that was the result of the preprocessing under the first condition was used as the initial structure of the preprocessing under the following condition.

After the preprocessing was performed as described above, the binding free energy of tankyrase 2 and XAV-939 was calculated by a method using the alchemical pathway calculation method based on the molecular dynamics calculation. The molecular dynamics calculation for calculating the binding free energy was performed with a simulation time of 140 ns under a fixed temperature and pressure condition (NPT ensemble). The data obtained by performing the molecular dynamics calculation were analyzed by the multi-state Bennett acceptance ratio (MBAR) method to calculate the binding free energy. The result is indicated in Table 1.

In Example 1, as a force field for the molecular dynamics calculation, AMBER ff14SB was used for tankyrase 2 and a general AMBER force field (GAFF) was used for XAV-939.

Comparative Example 1

In Comparative Example 1, the initial structure of the complex of tankyrase 2 and XAV-939 produced by the same procedure as in Example 1 was used as the binding structure corresponding to the state of (0, 1, 1) in FIG. 2. Next, the preprocessing for the binding free energy calculation was carried out in order of the states of (1, 1, 1), (1, 0, 1), and (1, 0, 0) by using the prepared binding structure corresponding to the state of (0, 1, 1). The binding free energy was calculated in the same manner as in Example 1 except for the above parts. The result is indicated in Table 1.

TABLE 1

|  | Binding Free Energy (kcal/mol) |
| --- | --- |
| Example 1 | −11.8 |
| Comparative Example 1 | −16.5 |
| Experimental Value | −11.0 |

The experimental value in Table 1 indicated above was calculated by referring to the paper (T. Karlberg et al., "Structural Basis for the Interaction between Tankyrase-2 and a Potent Wnt-Signaling Inhibitor", J. Med Chem., 53, 5352 (2010).) in which the activity value (dissociation constant) $K_d$ of tankyrase 2 and XAV-939 was described.

The above paper describes that the activity value $K_d$ of tankyrase 2 and XAV-939, measured using an isothermal titration calorimetry (ITC) apparatus, is 8±3 nM. The binding free energy $\Delta G°_{bind}$ has a relation, which is expressed by the following equation, with the activity value $K_d$. $k_B$ represents the Boltzmann constant, T represents a temperature (K), and $C^\ominus$ represents a standard concentration (1 mol/L).

$$\Delta G^\circ_{bind} = k_B T \ln\left[\frac{1}{C^\ominus} \cdot K_d\right]$$

From the above equation, when the activity value $K_d$ is 8 nM, $\Delta G^\ominus_{bind}$ at room temperature may be calculated to be −11.0 kcal/mol.

Figure 16:
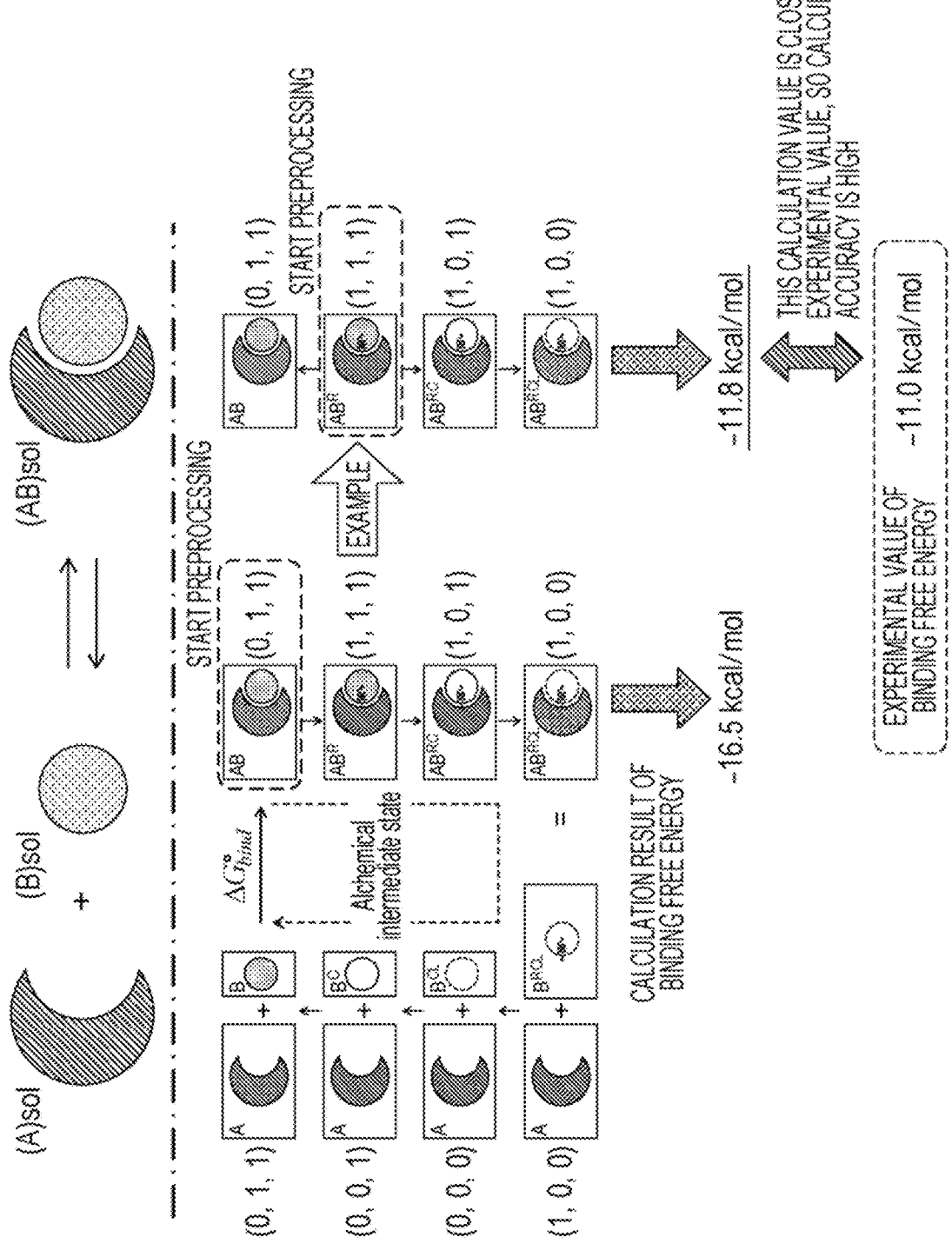
FIG. 16 is a diagram illustrating calculation procedures and calculation results of binding free energy in Example 1 and Comparative Example 1.

As indicated in Table 1, the result of Example 1 is closer to the experimental value than the result of Comparative Example 1. FIG. 16 illustrates a difference between the preprocessing procedures in Example 1 and Comparative Example 1 and the calculation results of the binding free energy in cases where the preprocessing was carried out in the respective procedures. In FIG. 16, as well as FIG. 2, the crescent shaped object indicates the target molecule (tankyrase 2) and the circular object indicates the candidate molecule (XAV-939).

From the above, it was confirmed that even when the binding state of the substances easily changes, it is possible to improve the calculation accuracy of the binding free energy by using the preprocessing method of the binding free energy calculation disclosed in the present disclosure.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A method of preprocessing, in information technology (IT) drug discovery, for calculating binding free energy between a first substance and a second substance by using a computer, the method comprising:
    obtaining a first binding structure of the first substance and the second substance under a condition where the second substance is constrained such that a binding state of the second substance to the first substance is maintained in a predetermined state; and
    obtaining a second binding structure of the first substance and the second substance by processing the first binding structure under a condition in which the second substance is not constrained, wherein
    the first substance is a target molecule of a drug, and the second substance is a candidate molecule whose binding property to the target molecule is evaluated.

2. The method according to claim 1, wherein
the target molecule is at least one of protein, ribonucleic acid (RNA), deoxyribonucleic acid (DNA), and the candidate molecule is at least one of a drug candidate molecule which becomes a drug candidate and a fragment which is used when a drug candidate molecule is designed.

3. The method according to claim 1, further comprising:
obtaining the binding structure by molecular dynamics calculation.

4. The method according to claim 1, further comprising:
performing constraint on the second substance by adding a constraint potential to the second substance.

5. The method according to claim 4, wherein
the constraint potential is a harmonic potential.

6. The method according to claim 4, wherein
obtaining the second binding structure under the condition where the second substance is not constrained by decreasing the constraint on the second substance in a stepwise manner.

7. The method according to claim 1, wherein
the binding free energy calculation is a calculation performed by an alchemical pathway calculation method.

8. The method according to claim 7, further comprising:
changing a parameter specifying, along a pathway of a thermodynamic cycle in the alchemical pathway calculation method, a state of the second substance in the pathway stepwise,
when binding structures are obtained under a condition where the parameter is a first numerical value and under a condition where the parameter is a second numerical value that is a numerical value next to the first numerical value in the path,
obtaining the first binding structure under the condition where the parameter is the first numerical value, and
obtaining, based on the first binding structure under the condition where the parameter is the first numerical value, the second binding structure under the condition where the parameter is the second numerical value.

9. The method according to claim 8, further comprising:
performing a plurality of calculations for obtaining the binding structure of the first substance and the second substance in parallel under conditions where the parameters are different from each other by using the computer capable of performing parallel processing.

10. The method according to claim 1, further comprising:
estimating the binding free energy between the first substance and the second substance based on the second binding structure; and
identifying candidate molecules for pharmaceutical products based on the estimating.

11. A method of binding free energy calculation, in information technology (IT) drug discovery, for calculating between a first substance and a second substance by using a computer, the method comprising:
    obtaining a first binding structure of the first substance and the second substance under a condition where the second substance is constrained such that it is possible to maintain a binding state of the second substance to the first substance in a predetermined state; and
    obtaining a second binding structure of the first substance and the second substance by processing the first binding under a condition in which the second substance is not constrained; and
    performing calculation for calculating the binding free energy based on the second binding structure,
    wherein the first substance is a target molecule of a drug, and the second substance is a candidate molecule whose binding property to the target molecule is evaluated.

12. The method according to claim 9, further comprising:
performing the calculation for calculating the binding free energy by an alchemical pathway calculation method.

13. The method according to claim 1, further comprising:
searching for candidates for a lead compound of the drug based on the obtained second binding structure.

\* \* \* \* \*